US006369222B1

(12) United States Patent
Binggeli et al.

(10) Patent No.: US 6,369,222 B1
(45) Date of Patent: Apr. 9, 2002

(54) MGLUR ANTAGONISTS AND A METHOD FOR THEIR SYNTHESIS

(75) Inventors: Alfred Binggeli, Binningen; Hans-Peter Maerki, Basel, both of (CH); Vincent Mutel, Mulhouse (FR); Wolfgang Wostl, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/902,916

(22) Filed: Jul. 11, 2001

(30) Foreign Application Priority Data

Jul. 18, 2000 (CH) .............................. 00115450

(51) Int. Cl.$^7$ ...................... C07D 403/04; C07D 409/04
(52) U.S. Cl. ...................... 540/577; 540/578; 540/580; 540/593
(58) Field of Search ................................. 544/296, 310, 544/319, 320; 540/577, 578, 580, 593

(56) References Cited

FOREIGN PATENT DOCUMENTS

| DE | 3820775 | 12/1989 |
|---|---|---|
| EP | 274 324 | 7/1988 |

OTHER PUBLICATIONS

Fréhel et al., J. Heterocyclic Chem., 22, pp. 1011–1016 (1985).

Pecherer et al., J. Heterocyclic Chem., 8(5), pp. 779–783 (1971).

Roglans et al., Synthetic Communications, 22(9), pp. 1249–1258 (1992).

Urban et al., Helv., 41, pp. 1806–1816 (1958).

Yamamoto et al., Bull. Chem. Soc. Jap., 44(1), pp. 153–158 (1971).

*Primary Examiner*—John M. Ford
(74) *Attorney, Agent, or Firm*—George W. Johnston; Dennis P. Tramaloni; F. Aaron Dubberley

(57) ABSTRACT

The invention relates to nitro- and cyano-1,2,4,5-tetrahydro-heterocycloazepinyl pyrimidine derivatives as well as their pharmaceutically acceptable salts. The invention further relates to medicaments containing such compounds and a process for the preparation of such compounds. The compounds of the invention are group I mGluR antagonists and are therefore useful for the control or prevention of acute and/or chronic neurological disorders.

71 Claims, No Drawings

MGLUR ANTAGONISTS AND A METHOD FOR THEIR SYNTHESIS

FIELD OF THE INVENTION

The present invention is concerned with novel mGluR antagonists, methods of their synthesis and the treatment and/or prevention of neurological disorders.

BACKGROUND OF THE INVENTION

In the central nervous system (CNS) the transmission of stimuli takes place by the interaction of a neurotransmitter sent out by a neuron, with a neuroreceptor on another neuron.

L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) belong to the second main group and, furthermore, belong to the family of G-protein-coupled receptors.

At present, eight different members of these mGluRs are known and some of these even have sub-types. On the basis of structural parameters, the different second messenger signaling pathways and their different affinity to low-molecular weight chemical compounds, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands, particularly antagonists, of metabotropic glutamate receptors belonging to the first group can be used for the treatment or prevention of acute and/or chronic neurological disorders such as epilepsy, stroke, chronic and acute pain, psychosis, schizophrenia, Alzheimer's disease, cognitive disorders and memory deficits.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, psychoses, anxiety, vomiting, dyskinesia and depression.

It is an object of the present invention to provide pharmaceutically active substances, medicaments and a method of their manufacture for the control or prevention of illnesses of the aforementioned kind. It is another object to provide radiolabeled mGluR1 receptor antagonists for use in binding assays.

SUMMARY OF THE INVENTION

It has surprisingly been found that the compounds of formula I are antagonists of metabotropic glutamate receptors of the first group:

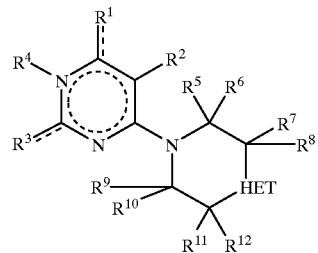

wherein $R^1$ signifies oxygen, hydroxy, lower alkoxy or 2,2,2-trifluoroethoxy;

$R^2$ signifies nitro or cyano;

$R^3$ signifies hydrogen, lower alkyl, oxygen, lower alkoxy, amino, lower alkyl-amino or hydroxy-lower alkyl-amino;

$R^4$ signifies hydrogen, lower alkyl, lower alkenyl, or is absent, if the adjacent nitrogen atom already is the origin of three bonds as —N= or =N—;

$R^5$, $R^6$, $R^9$ and $R^{10}$ signify, independently from each other, hydrogen or lower alkyl;

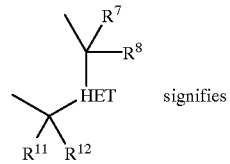 signifies

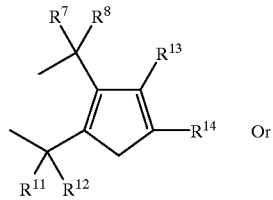

Or

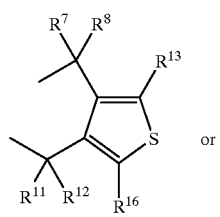

or

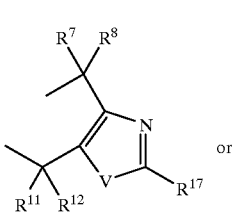

or

-continued

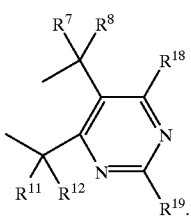
IId

R⁷, R⁸, R¹¹ or R¹² signify, independently from each other, hydrogen, lower alkyl, or hydroxy;
R¹³ and R¹⁴ signify, independently from each other, hydrogen or lower alkyl;
R¹⁵ and R¹⁶ signify, independently from each other, hydrogen or lower alkyl;
R¹⁷ signifies hydrogen, lower alkyl, lower alkoxy, hydroxy or amino;
R¹⁸ signifies hydrogen or hydroxy;
R¹⁹ signifies hydrogen, lower alkyl, lower alkoxy, hydroxy or amino;
V signifies NH, S or O; and
the dotted line may be a bond,
as well as with their pharmaceutically acceptable salts in their racemic and optically active form.

The present invention encompasses compounds of formula I and their pharmaceutically acceptable salts per se and as pharmaceutically active substances, their manufacture, medicaments based on a compound in accordance with the invention and their production as well as the use of the compounds in accordance with the invention in the control or prevention of illnesses of the aforementioned kind, and, respectively, for the production of corresponding medicaments. Furthermore, the use of radiolabeled mGluR1 receptor antagonists of formula I in a binding assay is also encompassed by the present invention.

The present invention is further illustrated by the following descriptions of preferred embodiments and examples. These preferred embodiments and examples are not limiting on the invention. One of skill in the arts of organic synthesis and/or pharmaceutical chemistry would well recognize a variety of obvious variations to these preferred embodiments and examples which would still be encompassed by this invention. The invention is limited only by the claims that follow and their equivalents.

DETAILED DESCRIPTION OF THE PREFERRED EMBODIMENTS

Compounds of formula I'

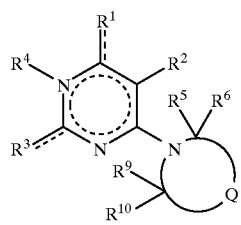
I' wherein
R¹ is oxygen, hydroxy, lower alkoxy or 2,2,2-trifluoroethoxy;
R² is nitro or cyano;
R³ is hydrogen, lower alkyl, oxygen, lower alkoxy, amino, lower alkyl-amino or hydroxy-lower alkyl-amino;
R⁴ is hydrogen, lower alkyl, lower alkenyl or is absent, if the adjacent nitrogen atom is part of a covalent double bond;
R⁵, R⁶, R⁹ and R¹⁰ are, independently from each other, hydrogen or lower alkyl;

is selected from the group consisting of

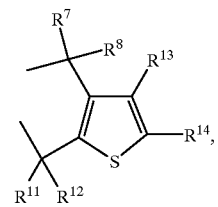
IIa

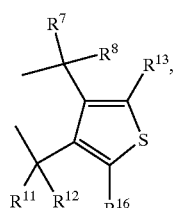
IIb

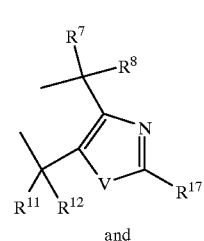
IIc and

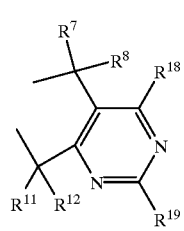
IId wherein
R⁷, R⁸, R¹¹ or R¹² are, independently from each other, hydrogen, lower alkyl, or hydroxy;
R¹³ and R¹⁴ are, independently from each other, hydrogen or lower alkyl;
R¹⁵ and R¹⁶ are, independently from each other, hydrogen or lower alkyl;
R¹⁷ is hydrogen, lower alkyl, lower alkoxcy, hydroxy or amino;
R¹⁸ is hydrogen or hydroxy;
R¹⁹ is hydrogen, lower alkyl, lower alkoxy, hydroxy or amino;

V is NH, S or O; and a dotted line is an optional bond, and pharmaceutically acceptable salts of a compound of formula I' are antagonists of mGluR.

Formula I' defines the same set of compounds as formula I. The compounds encompassed by Formula I' may be sub-divided into compounds of formulas I'a, I'b and I'c:

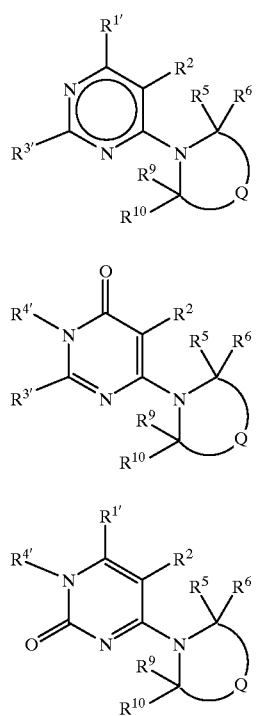

wherein $R^{1'}$ is hydroxy, lower alkoxy or 2,2,2-trifluoroethoxy;

$R^{3'}$ is hydrogen, lower alkyl, lower alkoxy, amino, lower alkyl-amino or hydroxy-lower alkyl-amino;

$R^{4'}$ is hydrogen, lower alkyl or lower alkenyl; and $R^2$, $R^5$, $R^6$, $R^9$, $R^{10}$ and

are as defined for formula I'.

Preferred compounds of formulas I, I', I'a, I'b and I'c in the scope of the present invention are those in which $R^2$ is $NO_2$.

Further preferred are compounds of formula I in the scope of the present invention, wherein $R^1$ is =O or lower alkoxy and HET represents a thiophene group.

The following are examples of such compounds:

[rac]-6-(4-Hydroxy-4,5,7,8-tetrahydro-thieno[2,3-d] azepin-6-yl)-2-methyl-5-nitro-3H-pyrimidin-4-one, 2-Methyl-5-nitro-6-(4,5,7,8-tetrahydro-thieno[2,3-d] azepin-6-yl)-3H-pyrimidin-4-one, 6-(6-Ethoxy-2-methyl-5-nitro-pyrimidin-4-yl)-5,6,7,8-tetrahydro-4H-thieno[2,3-d]azepine, or 3-Ethyl-2-methyl-5-nitro-6-(4,5,7,8-tetrahydro-thieno [2,3-d] azepin-6-yl)-3H-pyrimidin-4-one.

Also preferred are compounds of formula I in the scope of the present invention, wherein $R^1$ is =O or lower alkoxy, and HET represents a thiazole group.

The following are examples of such compounds:

2-Methyl-6-(2-methyl-4,5,7,8-tetrahydro-thiazolo[4,5-d] azepin-6-yl)-5-nitro-3H-pyrimidin-4-one, 6-(6-Ethoxy-2-methyl-5-nitro-pyrimidin-4-yl)-2-methyl-5,6,7,8-tetrahydro-4H-thiazolo[4,5-d]azepine, 3-Ethyl-2-methyl-6-(2-methyl-4,5,7,8-tetrahydro-thiazolo[4,5-d]azepin-6-yl)-5-nitro-3H-pyrimidin-4-one, 6-(2-Amino-4,5,7,8-tetrahydro-thiazolo[4,5-d]azepin-6-yl) -2-methyl-5-nitro-3H-pyrimidin-4-one, 6-(2-Amino-4,5,7,8-tetrahydro-thiazolo [4,5-d]azepin-6-yl)-3-ethyl-2-methyl-5-nitro-3H-pyrimidin-4-one, or 2-Methyl-5-nitro-6-(4,5,7,8-tetrahydro-thiazolo[4,5-d] azepin-6-yl)-3H-pyrimidin-4-one.

Further preferred compounds of formula I in the scope of the present invention are those, in which $R^1$ is hydroxy and HET represents a pyrimidine group.

The following are examples of such compounds:

7-(6-Hydroxy-2-methyl-5-nitro-pyrimidin-4-yl)-2-methyl-6,7,8,9-tetrahydro- 5H-pyrimido[4,5-d]azepin-4-ol, or 2-Methyl-5-nitro-6-(5,6,8,9-tetrahydro-pyrimido[4,5-d] azepin-7-yl)-pyrimidin-4-ol.

The term "lower alkyl" used in thee present description denotes straight-chain or branched saturated hydrocarbon residues with 1–7 carbon atoms, preferably with 1–4 carbon atoms, such as methyl, ethyl, n-propyl, i-propyl and the like.

The term "lower alkenyl" used in the present description denotes straight-chain or branched unsaturated hydrocarbon residues with 2–7 carbon atoms, preferably with 2–4 carbon atoms.

The term "lower alkoxy" denotes a lower alkyl residue in the sense of the foregoing definition bonded via an oxygen atom.

The term "pharmaceutically acceptable salt" denotes conventional acid-addition salts or base-addition salts which retain the biological effectiveness and propertied of the compounds of formulae I, I', I'a, I'b and/or I'c and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methane-sulfonic acid, oxalic acid, succinic acid, citric acid, malic acid, lactic acid, fumaric acid and the like. Sample base-addition salts include those derived from ammonium, potassium, sodium and quaternary ammonium hydroxides, such as tetramethylammonium hydroxide.

The compounds of formula I and their pharmaceutically acceptable salts can be manufactured by reacting a compound of the formula

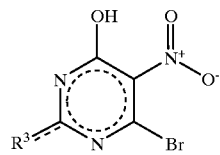

with a compound of formula

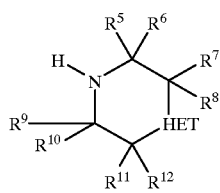

to a compound of formula

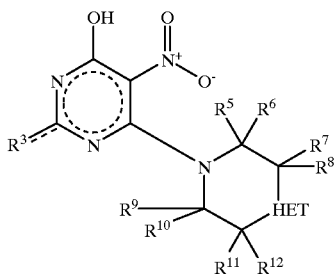

I-1 wherein $R^3$ and $R^5$ to $R^{12}$ have the significance given above.

reacting a compound of formula

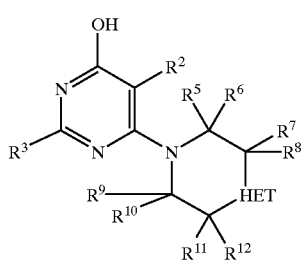

I-2 to a compound of formula

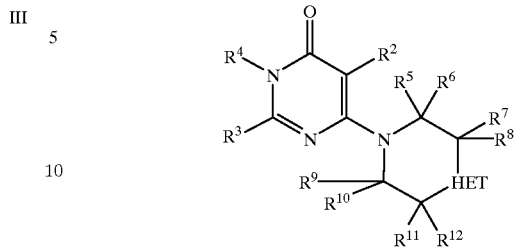

I-3 or to a compound of formula

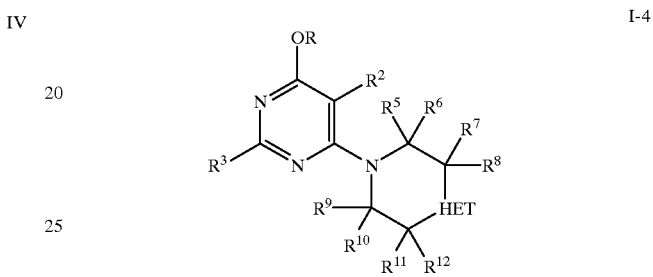

I-4 wherein $R^2$, $R^3$ and $R^5$ to $R^{12}$ have the significance given above and R signifies hydrogen or lower alkyl, or reacting a compound of formula

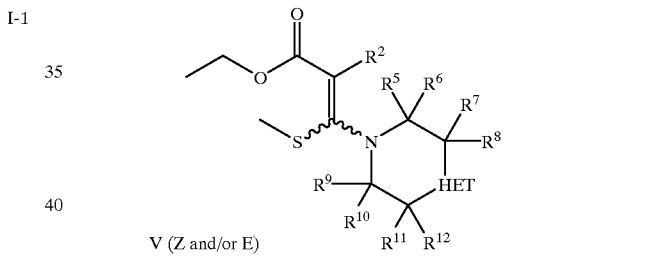

V (Z and/or E)

with a compound of formula

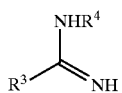

VIa to a compound of formula

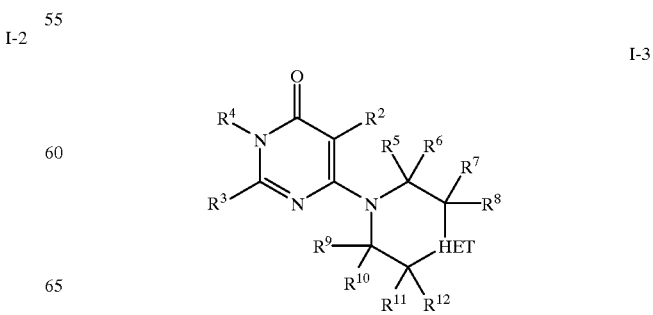

I-3 wherein the substituents have the significance given above, and, if desired, converting a functional group in a compound of formula I into another functional group and, if desired, converting a compound of formula I into a pharmaceutically acceptable salt. The conversion of one functional group into another functional group and the formation and isolation of pharmaceutically acceptable salts can each be carried out according to methods known in the art.

In the following schemes I to VII and in Examples 1–10 the reaction steps and reaction variants a)–c) are described in more detail.

Chloro-methoxy-nitro pyrimidines VII (Scheme I) are known [e.g. 6-chloro-4-methoxy-2-methyl-5-nitro-pyrimidine: Helv. (1958), 41, 1806]. Treatment of the 2-alkyl 6-chloro-4-methoxy-5-nitro-pyrimidines VII with hydrobromic acid in acetic acid preferentially at temperatures between 0° C. and 60° C. gives the 2-alkyl-6-bromo-5-nitro-3H-pyrimidin-4-ones III (Scheme I).

Scheme I

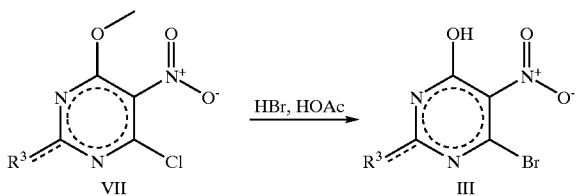

The 2-alkyl-6-bromo-5-nitro-3H-pyrimidin-4-ones III react with optionally substituted secondary amines IV in the presence of a base like triethylamine in solvents like N,N-dimethylformamide, dimethylsulfoxide, acetone, methyl-ethylketone or tetrahydrofuran at temperatures between 0° C. and 100° C. to the tertiary amines I-1 (Scheme II). A method of preparing an optionally substituted secondary amines according to formula IV is exemplified in the Examples found below, and one of skill in the art of organic synthesis would be able to form other compounds according to formula IV from this example and their knowledge of the art.

Scheme II

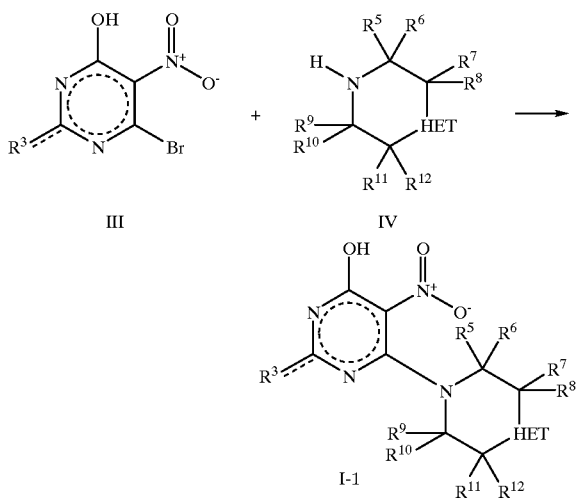

Bis(methylthio)-acrylates VIII react with optionally substituted secondary amines IV in the presence of bases like potassium carbonate and/or triethylamine in solvents like ethanol, methanol, acetone or methyl-ethylketone at temperatures between room temperature and 100° C. to adducts V, which can be formed as Z-isomer, as mixture of E and Z isomers or as E isomer (Scheme III). Bis(methylthio)-acrylates are well known in the chemical literature and many are commercially available; e.g. ethyl 2-cyano-3,3-bis (methylthio)acrylate is commercially avialable from TCI America. Adducts V can be reacted with amidines, urea or thiourea derivatives VI and VIa either in the presence of 1,8-diazabicyclo[5.4.0]undec-7-ene (commercially available from suppliers like Aldrich and Fluka) in N,N-dimethylformamide or dimethylsulfoxide at temperatures between 70° C. and 140° C. or in the presence of sodium ethylate in ethanol preferentially at reflux thus yielding pyrimidineoles I-2 or pyrimidinones I-3.

Scheme III

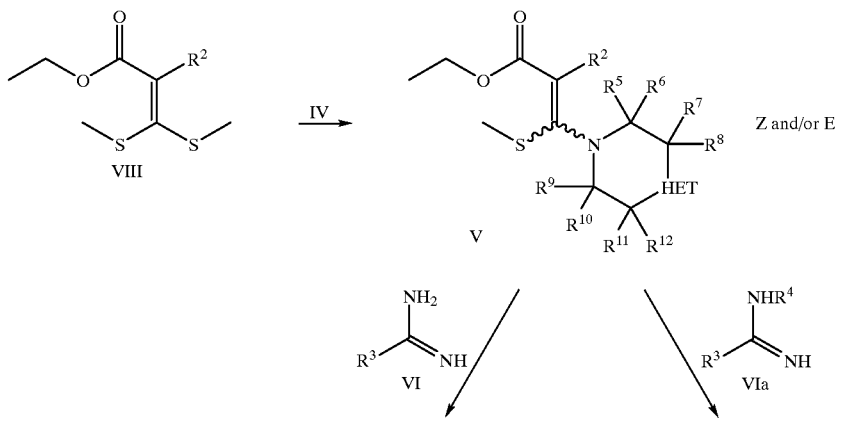

-continued

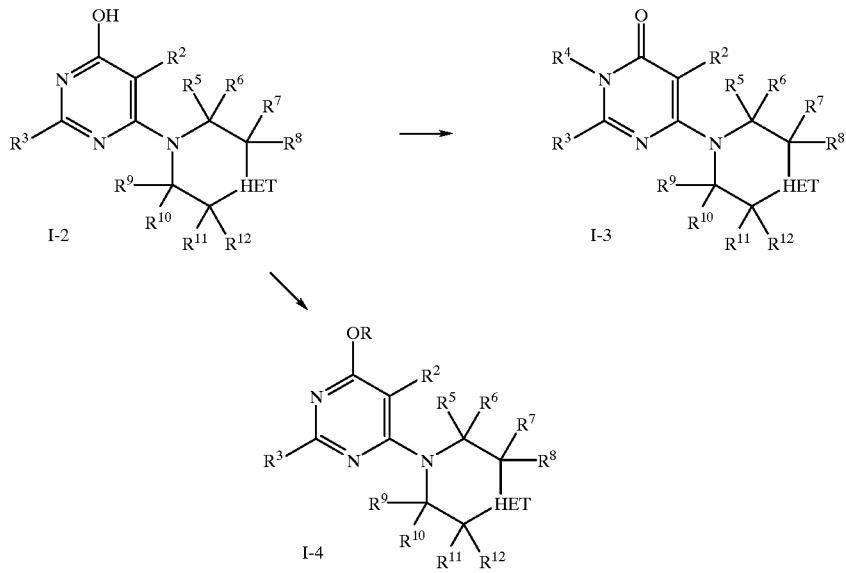

Alkylation of adducts I-2 with $R^2$ being a cyano or a nitro group (Scheme III) using optionally substituted alkyl halides, tosylates, mesylates or trifluoro-methanesulfonates in solvents like ethanol, methanol, dichloromethane, chloroform, N,N-dimethylformamide, dimethylsulfoxide, acetone, methyl-ethylketone or tetrahydrofuran in the presence of a base like alkali carbonates, e.g. sodium, potassium or cesium carbonate, tertiary amines like triethylamine or ethyl-diisopropylamine, alkali methyl hydrides, like sodium or potassium hydride, or phase transfer catalysts like benzyl-trimethylammonium chloride in the presence of solid or concentrated aqueous sodium hydroxide gives variable mixtures of N-and/or O-alkylated products I-3 and I-4.

Azepines IV-1 condensed to a heteroaromatic 5-membered ring bearing two heteroatoms can be prepared from bromoazepinones IX (Scheme IV) as e.g. 4-bromo-5-oxo-azepane-1-carboxylic acid tert.-butyl ester (prepared from 5-bromo-azepan-4-one hydrobromide (1:1) [Ger. Offen. (1989), DE 3820775] with di-tert.-butyldicarbonate in dioxane/aq. sodium hydrogen carbonate solution at room temperature) by reaction with an amide, a thioamide, an urea or a thiourea compound X in a solvent like ethanol, dioxane or acetonitrile in the presence of a base like sodium ethylate or triethylamine at temperatures between room temperature and 120° C. followed by removal of the tert.-butoxy carbonyl function with acid, e.g. with hydrogen chloride (aqueous, 37%) in methanol at temperatures between room temperature and 80° C. Other species of bromoazepinones IX can be prepared by one of skill in the art of organic synthesis by analogy with knowledge well-known in the art.

Scheme IV

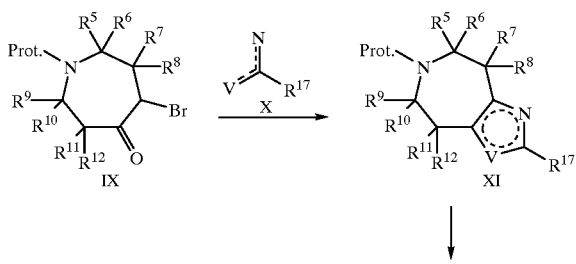

-continued

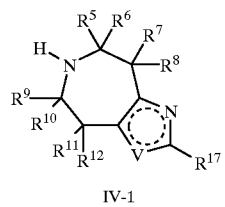

IV-1

Azepines IV-2 condensed to a heteroaromatic 6-membered ring bearing two heteroatoms can be prepared from alkoxycarbonyl-azepinones XII as e.g. 4-ethoxy-carbonyl-5-oxo-azepane-1-carboxylic acid tert.-butyl ester [Synthetic Communications 22 (1992), 1249-1258] (Scheme V) by condensation with an amidine XIII in a solvent like ethanol, dioxane or N,N-dimethylformamide in the presence of a base like sodium ethoxide or potassium tert.-butylate at temperatures between 40° C. and 110° C. Other species of alkoxycarbonyl-azepinones XII can be prepared by one of skill in the art of organic synthesis by analogy with knowledge well-known in the art. The primarily formed compounds XIVa can be further modified by transformation of the hydroxy function into a leaving group, e.g. a trifluorosulfonyloxy function with trifluorosulfonic acid anhydride and a base like triethylamine in an inert solvent like dichloromethane at temperatures between −40° C. and 60° C., thus giving compounds XIVb. The trifluorosulfonyloxy function in compounds XIVb can then be replaced by a hydrazine moiety by reacting it with hydrazine in a solvent like ethanol preferentially at reflux giving compounds XIVc. Hydrazino-compounds XIVc can be transformed by silver oxide in ethanol at reflux into the compounds XIVd, a sequence as described in [Bull. Chem. Soc. Jap. (1971), 44(1), 153-8]. Removal of the tert.-butoxy carbonyl function in compounds XIVa or XIVd with acid, e.g. with hydrogen chloride (aqueous, 37%) in methanol at temperatures between room temperature and 80° C. gives then the azepines IV-2.

Scheme V

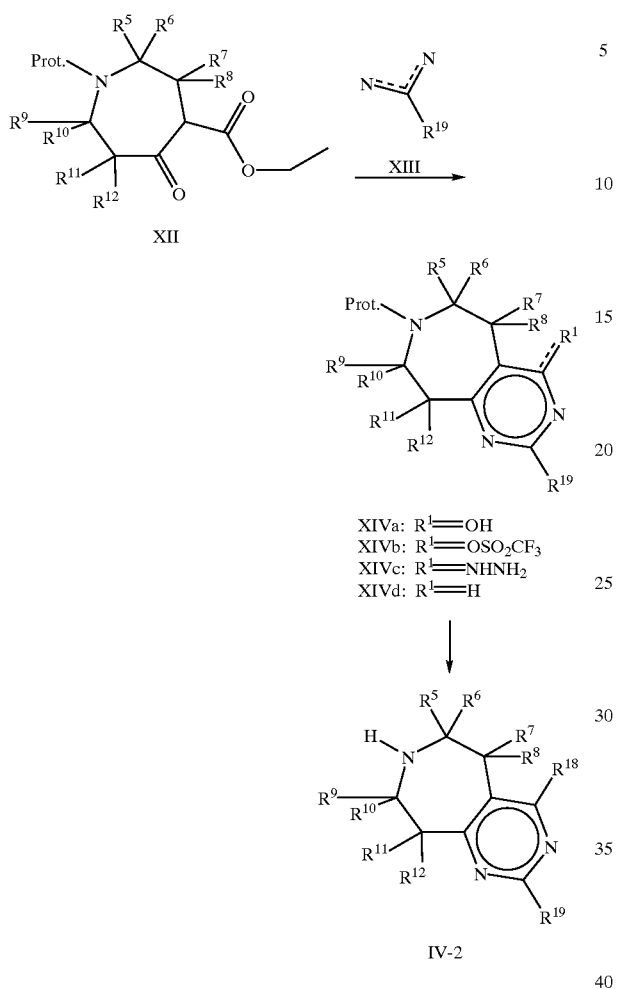

XIVa: R¹=OH
XIVb: R¹=OSO₂CF₃
XIVc: R¹=NHNH₂
XIVd: R¹=H

IV-2

5,6,7,8-Tetrahydro-4H-thieno[2,3-d]azepines IV-3 and IV-5 with or without a hydroxy function at the carbon attached to the thieno moiety are known [J. Heterocyclic Chem. 22, 1011 (1985)]. Precursor acid chlorides XV [J. Heterocyclic Chem. 22, 1011 (1985)] bearing preferentially a tosyloxy protective function at the azepine secondary nitrogen function are cyclized in an inert solvent like 1,2-dichloroethane, dichloromethane or nitrobenzene in the presence of a Lewis acid catalyst like aluminium trichloride, tin tetrachloride or phosphorous pentachloride at temperatures between −40° C. and 80° C. to yield the protected ketones XVI. Keto thieno[2,3-d]azepines IV-4 are then prepared by cleavage of N-tosyl function with hydrobromic acid in the presence of a scavenger reagent like phenol in a solvent like ethyl acetate at room temperature, whereas hydroxy thieno[2,3-d]azepines IV-3 can be obtained by simultaneous reduction of the keton function and removal of the N-tosyl protective function by treatment with sodium bis(methoxyethoxy)aluminium-hydride in toluene at reflux. The hydroxy thieno[2,3-d]azepines IV-3 can be further reduced to 5,6,7,8-tetrahydro-4H-thieno[2,3-d]azepines IV-5 with stannous chloride in acetic acid in the presence of hydrochloric acid at temperatures between room temperature and 100° C.

5,6,7,8-Tetrahydro-4H-thieno[3,4-d]azepines IV-6 isomeric to 5,6,7,8-tetrahydro-4H-thieno[2,3-d]azepines IV-5 can be prepared from 2-thiophen-3-yl-ethylamine derivatives XVII [Eur. Pat. Appl. (1988), EP 274324 A1] in an analogous sequence as described for the thieno[2,3-d] azepines outlined in detail in Scheme VI.

Scheme VI

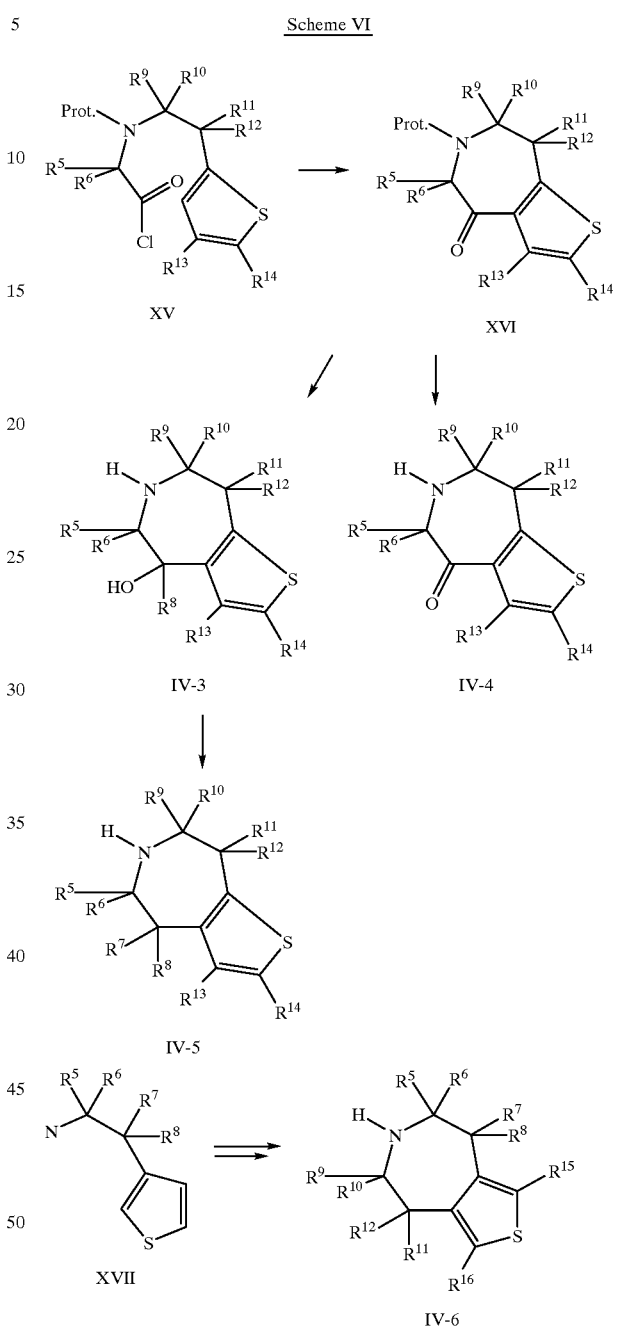

A labeled compound, for example 1-ethyl-2-methyl-6-oxo-4-(1,1,2-tritritio-1,2,4,5-tetrahydro-benzo[d]azepin-3-yl)-1,6-dihydro-pyrimidine-5-carbonitrile, is needed for the binding assay for the characterization of mGluR 1 antagonistic properties and can be prepared according to synthesis schemes I–III starting from a labeled amine as the 1,1,2-tritritio-2,3,4,5-tetrahydro-1H-benzo[d]azepine XXI which can be prepared as outlined in Scheme VII. The 1-(5-bromo-1,2-dihydro-benzo[d]azepin-3-yl)-ethanone XIX can be obtained by reaction of the 1-(1,2,4,5-tetrahydro-benzo[d]azepin-3-yl)-ethanone XVIII [J. Heterocyci. Chem. (1971), 8(5), 779–83] with N-bromosuccinimide in carbon tetrachloride in the presence of a radical initiator like dibenzoylperoxide or 1,1'-azobis-(cyclohexanecarbonitrile) preferentially at reflux. Hydrogenation of the 1-(5-bromo-1,2-dihydro-benzo[d]azepin-3-yl)-ethanone XIX with tritium gas using a palladium or platinum catalyst in solvents methanol, ethanol or an ether like tetrahydrofuiran preferentially in the presence of a base like triethylamine gives the 1-(1,1,2-tritritio-1,2,4,5-tetrahydro-benzo[d]azepin-3-yl)-ethanone XX which can be converted into the 1-(1,1,2-tritritio-1,2,4,5-tetrahydro-benzo[d]azepin-3-yl)-ethanone XXI with conc. aq. hydrochloric acid in methanol.

Scheme VII

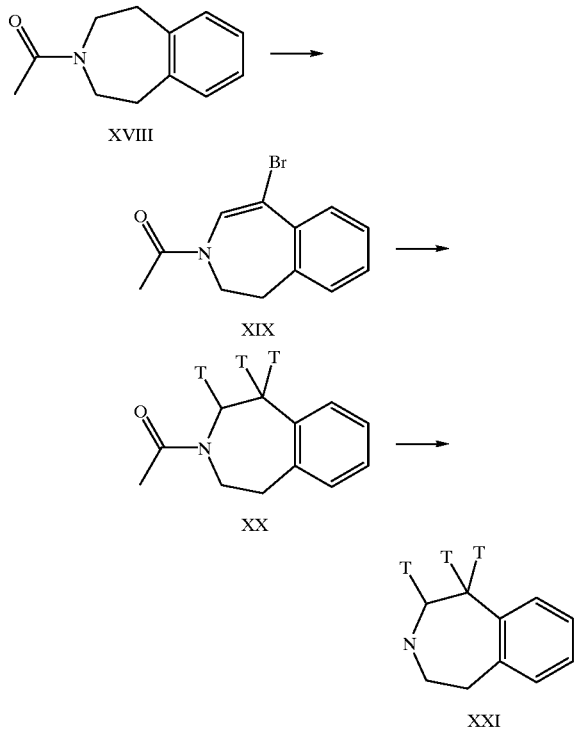

The pharmaceutically acceptable salts can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds of formula I.

The compounds of formula I and their pharmaceutically acceptable salts are, as already mentioned above, metabotropic glutamate receptor antagonists and can be used for the treatment or prevention of acute and/or chronic neurological disorders, such as epilepsy, stroke, chronic and acute pain, psychosis, schizophrenia, Alzheimer's disease, cognitive disorders, memory deficits and psychosis. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression.

The compounds of the present invention are group I mGluR antagonists and were tested using the following method:

Binding Assay for the Characterization of mGluR 1 Antagonistic Properties

Binding assay with tritiated 1-ethyl-2-methyl-6-oxo-4-(1,1,2-tritritio-1,2,4,5-tetrahydro-benzo[d]azepin-3-yl)-1,6-dihydro-pyrimidine-5-carbonitrile: HEK 293 cells were transiently transfected with the rat mGluR1a receptor. The cells were collected and washed 3 times with PBS. The cell pellets were frozen at −80° C. Membranes were prepared from HEK 293 cells transfected with the rat mGluR1a receptor and used in the binding experiments at 10 μg proteins per assay after resuspension in a HEPES NaOH 20 mM, pH=7.4 binding buffer. 1-Ethyl-2-methyl-6-oxo-4-(1,1,2-tritritio-1,2,4,5-tetrahydro-benzo[d]azepin-3-yl)-1,6-dihydro-pyrimidine-5-carbonitrile (S.A. 33.4 Ci/mmol) was used at 3 nM final concentration. The incubation with variable concentrations of potential inhibitors was performed for 1 hour at room temperature, the incubate was then filtered onto GF/B glass fiber filter preincubated 1 hour in PEI 0,1% and washed 3 times with 1 ml of cold binding buffer. The radioactivity retained on the unifilter 96 was counted using a Topcount β counter. After correction for non specific binding the data were normalized and the $IC_{50}$ value calculated using a 4 parameters logistic equation which was fitted to the inhibition curve.

Preferred compounds have an $IC_{50}$ range of 0.001–50.00 μM (B-$IC_{50}$).

In the table below are shown some specific activity data of preferred compounds:

| | Example No. | B-$IC_{50}$ (μM) |
|---|---|---|
| 2-methyl-6-(2-methyl-4,5,7,8-tetrahydro-thiazolo[4,5-d]azepin-6-yl)-5-nitro-3H-pyrimidin-4-one | 1 | 30 |
| 6-(6-ethoxy-2-methyl-5-nitro-pyrimidin-4-yl)-2-methyl-5,6,7,8-tetrahydro-4H-thiazolo[4,5-d]azepine | 2 | 4.2 |
| 3-ethyl-2-methyl-6-(2-methyl-4,5,7,8-tetrahydro-thiazolo[4,5-d]azepin-6-yl)-5-nitro-3H-pyrimidin-4-one | 2 | 2.1 |
| 6-(2-amino-4,5,7,8-tetrahydro-thiazolo[4,5-d]azepin-6-yl)-2-methyl-5-nitro-3H-pyrimidin-4-one | 3 | 49 |
| 6-(2-amino-4,5,7,8-tetrahydro-thiazolo[4,5-d]azepin-6-yl)-3-ethyl-2-methyl-5-nitro-3H-pyrimidin-4-one | 4 | 6 |
| 2-methyl-5-nitro-6-(4,5,7,8-tetrahydro-thiazolo[4,5-d] azepin-6-yl)-3H-pyrimidin-4-one | 6 | 43 |
| 2-methyl-5-nitro-6-(4,5,7,8-tetrahydro-thieno[2,3-d]azepin-6-yl)-3H-pyrimidin-4-one | 9 | 1.9 |

-continued

| Example No. | B-IC$_{50}$ ($\mu$M) |
|---|---|
| 6-(6-ethoxy-2-methyl-5-nitro-pyrimidin-4-yl)-5,6,7,8-tetrahydro-4H-thieno[2,3-d]azepine | 10 | 0.44 |
| 3-ethyl-2-methyl-5-nitro-6-(4,5,7,8-tetrahydro-thieno[2,3-d]azepin-6-yl)-3H-pyrimidin-4-one | 10 | 0.069 |

The compounds of formula I and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or anti-oxidants. They can also contain still other therapeutically valuable substances.

As mentioned earlier, medicaments containing a compound of formula I or a pharmaceutically acceptable salt thereof and a therapeutically inert excipient are also encompassed by the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

Finally, as mentioned earlier, the use of compounds of formula I and of pharmaceutically acceptable salts thereof for the production of medicaments, especially for the control or prevention of acute and/or chronic neurological disorders of the aforementioned kind, is also apart of the invention.

EXAMPLE 1

2-Methyl-6-(2-methyl-4,5,7,8-tetrhydro-thiazolo[4,5-d]azepin-6-yl) -5-nitro-3H-pyrimidin-4-one 6-Bromo-2-methyl-nitro-3H-pyrimidin-4-one 56.6 ml (503 mmol) of hydrobromic acid solution (48% in water) were added dropwise to a solution of 20.5 g (101 mmol) of the 2-methyl-4-methoxy-5-nitro-6-chloro-pyrimidine [Helv. (1958), 41, 1806] in 450 ml of acetic acid and the reaction mixture was stirred at room temperature for 44 hours. It was then evaporated under reduced pressure and the residue formed poured into 500 ml of an ice/water mixture and extracted 3 times with 500 ml of dichloromethane. The combined dichloromethane phases were washed with 100 ml of water and evaporated under reduced pressure. There were thus obtained 16.3 g (69.6 mmol, yield 69%) of the 6-bromo-2-methyl-5-nitro-3H-pyrimidin-4-one as light yellow solid, which was used without further purification.

2-methyl-5,6,7,8-tetrhydro-4H-thiazolo[4,5-d]azepine

The title compound was prepared by the following reaction sequence: i) treatment of the 5-bromo-azepan-4-one hydrobromide (1:1) [Ger. Offen. (1989), DE 38207751] with di-t-butyldicarbonate in dioxane/aq. sodium hydrogen carbonate solution to yield the 4-bromo-5-oxo-azepane-1-carboxylic acid tert-butyl ester; ii) treatment of the 4-bromo-5-oxo-azepane-1-carboxylic acid tert-butyl ester with thioacetamide in ethanol in the presence of triethylamine at reflux to give the 2-methyl-4,5,7,8-tetrahydro-thiazolo[4,5-d]azepine-6-carboxylic acid tert-butyl ester; iii) conversion of the 2-methyl-4,5,7,8-tetrahydro-thiazolo[5-d]azepine-6-carboxylic acid tert-butyl ester into the 2-methyl-5,6,7,8-tetrahydro-4H-thiazolo[4,5-d]azepine by removal of the tert-butyloxycarbonyl function with hydrogen chloride (aqueous, 37%) in methanol at room temperature.

2-Methyl-6-(2-methyl-4,5,7,8-tetrahydro-thiazolo[4,5-d]azepine-6-yl)-5-nitro-3H-pyrimidin-4-one A suspension of 0.234 g (1.00 mmol) of the 6-bromo-2-methyl-5-nitro-3H-pyrimidin-4-one, 0.205 g (1.00 mmol) of the 2-methyl-5,6,7,8-tetrahydro-4H-thiazolo[4,5-d]azepine hydrochloride and 0.304 g (2.20 mmol) of potassium carbonate in 2.0 ml of N,N-dimethylformamide was stirred at room temperature for 60 hours. The reaction mixture was then poured into 50 ml of an ice/water mixture and the crystals formed collected by filtration. Thus, a first crop of the 2-methyl-6-(2-methyl-4,5,7,8-tetrahydro-thiazolo[4,5-d]azepin-6-yl)-5-nitro-3H-pyrimidin-4-one was obtained. The mother liquor was then evaporated and the residue chromatographed on silica gel using a 9:1 v/v mixture of dichloromethane and methanol as eluent giving a second crop of the 2-methyl-6-(2-methyl- 4,5,7,8-tetrahydro-thiazolo[4,5-d]azepin-6-yl)-5-nitro-3H-pyrimidin-4-one, in total 0.252 g (0.785 mmol, yield 78.5%) as light yellow solid; m.p. >200° C.; MS: [M+H]$^+$=322.

EXAMPLE 2

6-(6-Ethoxy-2-methyl-5-nitro6-pyrimidin-4-yl)-2-methyl-5,6,7,8-tetrahydro-4H-thiazolo[4,5-d]azepine and 3-Ethyl-2-methyl-6-(2-methyl-4,5,7,8-tetrahydro-thiazolo[4,5-d]azepin-6-yl)-5-nitro-3H-pyrimidin-4-one A suspension of 0.120 g (0.373 mmol) of 2-methyl-6-(2-methyl-4,5,7,8-tetrahydro-thiazolo[4,5-d]azepin-6-yl)-5- nitro-3H-pyrimidin-4-one (example 1), of 0.070 g (0.45 mmol) of the ethyl iodide and of 0.077 g (0.56 mmol) of potassium carbonate in 1.0 ml of N,N-dimethylformamide was stirred at room temperature for 4 hours. The reaction mixture was then poured into 50 ml of an ice/water mixture and extracted 3 times with 50 ml of ethylacetate. The combined ethylacetate phases were dried over magnesium sulfate and evaporated under reduced pressure. The residue formed was then chromatographed on silica gel using a 95:5 v/v mixture of dichloromethane and methanol as eluent giving in a first fraction 0.025 g (0.072 mmol, yield 19%) of the 6-(6-ethoxy-2-methyl-5-nitro-pyrimidin-4-yl)-2-methyl-5,6,7,8-tetrahydro-4H-thiazolo[4,5-d]azepine as yellow amorphous solid; MS: [M+H]$^+$=350.

The second fraction provided 0.081 g (0.23 mmol, yield 62%) of the 3-ethyl-2-methyl-6-(2-methyl-4,5,7,8-tetrahydro-thiazolo[4,5-d]azepin-6-yl) -5-nitro-3H-pyrimidin-4-one as yellow solid after crystallization from ether; m.p. 164.2–166.8° C.; MS: [M+H]$^+$=350.

EXAMPLE 3

6-(2-Amino-4,5,7,8-tetrahydro-thiazolo[4,5-d]azepin-6-yl)-2-methyl-5-nitro-3H-pyrimidin-4-one In analogy to the procedure described in example 1c 6-bromo-2-methyl-5-nitro-3H-pyrimidin-4-one as prepared in example 1a was treated with 2-amino-5,6,7,8-tetrahydro-4H-thiazolo[4,5-d]azepine [Ger. Offen. (1989), DE 3820775] in N,N-dimethylformamide in the presence of potassium carbonate at 110° C. to yield the title compound as yellow solid; m.p. >200° C.; MS: [M+H]$^+$=323.

EXAMPLE 4

6-(2-Amino-4,5,7,8-tetrahydro-thiazolo[4,5-d]azepin-6-yl)-3-ethyl-2-methyl-5-nitro-3H-pyrimidin-4-one In analogy to the procedure described in example 2 the 6-(2-amino-4,5,7,8-tetrahydro-thiazolo[4,5-d]azepin-6-yl)-2-methyl-5-nitro-3H-pyrimidin-4-one (example 3) was treated with the ethyl iodide in N,N-dimethylformamide in the presence of potassium carbonate at room temperature to yield the title compound as yellow solid; m.p.>200° C.; MS: [M+H]$^+$=351.

EXAMPLE 5

7-(6-Hydroxy-2-methyl-5-nitro-pyrimidin-4-yl)-2-methyl-6,7,8,9-tetrahydro-5H-pyrimido[4,5-d]azepin-4-ol In analogy to the procedure described in example 1c 6-bromo-2-methyl-5-nitro-3H-pyrimidin-4-one (example. 1a) was treated with the 2-methyl-6,7,8,9-tetrahydro-5H-pyrimido[4,5-d]azepin-4-ol (prepared from the corresponding N-benzyl derivative [Bull. Chem. Soc. Jap. (1971), 44(1), 153–8] by catalytic hydrogenation with palladium on charcoal) in N,N-dimethylformamide in the presence of triethylamine at room temperature to yield the title compound as yellow solid; m.p.>200° C.; MS: [M+H]$^+$=333.

EXAMPLE 6

2-Methyl-5-nitro-6-(4,5,7,8-tetrahydro-thiazolo[4,5-d]azepin-6-yl)-3H-pyrimidin-4-one 5,6,7,8-tetrahydro-4H-thiazolo[4,5-d]azepine The title compound was prepared by the following reaction sequence: i) treatment of 4-bromo-5-oxo-azepane-1-carboxylic acid tert-butyl ester (example 1 b) with phosphorous pentasulfide, formamide and triethylamine in dioxane at reflux to yield 4,5,7,8-tetrahydro-thiazolo[4,5-d]azepine-6-carboxylic acid tert-butyl ester; ii) conversion of 4,5,7,8-tetrahydro-thiazolo[4,5-d]azepine-6-carboxylic acid tert-butyl ester into 5,6,7,8-tetrahydro-4H-thiazolo[4,5-d]azepine by removal of the tert-butyloxycarbonyl function with hydrogen chloride (aqueous, 37%) in methanol at room temperature.

b) 2-Methyl-5-nitro-6-(4,5,7,8-tetrahydro-thiazolo[4,5-d]azepin-6-yl)-3H-pyrimidin-4-one In analogy to the procedure described in example 1c 6-bromo-2-methyl-5-nitro-3H-pyrimidin-4-one (example 1a) was treated with the 5,6,7,8-tetrahydro-4H-thiazolo[4,5-d]azepine in N,N-dimethylformamide in the presence of potassium carbonate at room temperature to yield the 2-methyl-5-nitro-6-(4,5,7,8-tetrahydro-thiazolo[4,5-d]azepine-6-yl)-3H-pyrimidin-4-one as yellow amorphous solid; MS: (M–H)$^-$=306.

EXAMPLE 7

2-Methyl-5-nitro-6-(5,6,8,9-tetrahydro-pyrimido[4,5-d]azepin-7-yl)-pyrimidin-4-ol In analogy to the procedure described in example 1c 6-bromo-2-methyl-5-nitro-3H-pyrimidin-4-one (example 1a) was treated with 6,7,8,9-tetrahydro-5H-pyrimido[4,5-d]azepine trihydrochloride [Bull. Chem. Soc. Jap. (1971), 44(1), 153–8]in N,N-dimethylformamide in the presence of N-ethyl-di-isopropylamine at room temperature to yield the title compound as yellow solid; m.p.>200° C.; MS: [M–H]$^-$=301.

EXAMPLE 8

[rac]-6-(4-Hydroxy-4,5,7,8-tetrahydro-thieno[2,3-d]azepin-6-yl)-2-methyl-5-nitro-3H-pyrimidin-4-one In analogy to the procedure described in example 1c 6-bromo-2-methyl-5-nitro-3H-pyrimidin-4-one (example 1a) was treated with the [rac]-5,6,7,8-tetrahydro-4H-thieno[2,3-d]azepin-4-ol [J. Heterocycl. Chem. (1985), 22(4), 1011–16]in N,N-dimethylformamide in the presence of N-ethyl-di-isopropylamine at room temperature to yield the title compound as light yellow oil; MS: [M–H]$^-$=321.

EXAMPLE 9

2-Methyl-5-nitro-6-(4,5,7,8-tetrahydro-thieno[2.3-d]azepin-6-yl)-3H-pyrimidin-4-one According to the method described in example 1c 6-bromo-2-methyl-5-nitro-3H-pyrimidin-4-one (example 1a) was treated with 5,6,7,8-tetrahydro-4H-thieno-[2,3-d]azepine [J. Heterocycl. Chem. (1985), 22(4), 1011–16] in N,N-dimethylformamide in the presence of N-ethyl-di-isopropylamine at room temperature to yield the title compound as yellow solid; m.p.>200° C.; MS: [M–H]$^-$=305.

EXAMPLE 10

6-(6-Ethoxy-2-methyl-5-nitro-pyrimidin-4-yl)-5,6,7,8-tetrahydro-4H-thieno[2,3-d]azepine and 3-Ethyl-2-methyl-5-nitro-6-(4,5,7,8-tetrahydro-thieno[2,3-d]azepin-6-yl)-3H-pyrimidin-4-one In analogy to the procedure described in example 2 2-methyl-5-nitro-6-(4,5,7,8-tetrahydro-thieno[2,3-d]azepin-6-yl)-3H-pyrimidin-4-one (example 9) was treated with ethyl bromide in N,N-dimethylformamide in the presence of potassium carbonate at room temperature to yield 6-(6-ethoxy-2-methyl-5-nitro-pyrimidin-4-yl)-5,6,7,8-tetrahydro-4H-thieno[2,3-d]azepine as light yellow amorphous solid; MS: [M+H]$^+$=335; and 3-ethyl-2-methyl-5-nitro-6-(4,5,7,8-tetrahydro-thieno[2,3-d]azepin-6-yl)-3H-pyrimidin-4-one as yellow foam; MS: [M+H]$^+$=335.

Preparation of the Labeled Compound Needed for the Binding Assay

1-Ethyl-2-methyl-6-oxo-4-(1,1,2-tritritio-1,2,4,5-tetrahydro-benzo[d]azepin-3-yl)-1,6-dihydro-pyrimidine-5-carbonitrile 1,1,2-Tritritio-2,3,4,5-tetrahydro-1H-benzo[d]azepine The 1,1,2-tritritio-2,3,4,5-tetrahydro-1H-benzo[d]azepine was obtained by the following sequence:
reaction of the 1-(1,2,4,5-tetrahydro-benzo[d]azepin-3-yl)-ethanone [J. Heterocycl. Chem. (1971), 8(5), 779–831] with dibenzoylperoxide and N-bromosuccinimide in carbon tetrachloride at reflux yielded the 1-(5-bromo-1,2-dihydro-benzo[d]azepin-3-yl)-ethanone; hydrogenation of the 1-(5-bromo-1,2-dihydro-benzo[d]azepin-3-yl)-ethanone with tritium using Pd/C in methanol in the presence of triethylamine yielded the 1-(1,1,2-tritritio-1,2,4,5-tetrahydro-benzo [d]azepin-3-yl) -ethanone; treatment of the 1-(1,1,2-tritritio-1,2,4,5-tetrahydro-benzo[d]azepin-3-yl)-ethanone with conc. aq. hydrochloric acid in methanol gave the 1,1,2-tritritio-2,3,4,5-tetrahydro-1H-benzo[d]azepine.

E- and/or Z-2-cyano-3-methylsulfanyl-3-(1,1,2-tritritio-1,2,4,5-tetrahydro-benzo[d]azepin-3-yl)-acrylic acid ethyl ester A solution of 35 mg (0.16 mmol) of ethyl 2-cyano-3,3-bis(methylthio)acrylate, of 4.4 mg (0.024 mmol) of 1,1,2-tritritio-2,3,4,5-tetrahydro-1H-benzo[d]azepine hydrochloride, and of 10 mg (0.1 mmol) of triethylamine in 0.37 ml of ethanol was heated at reflux for 6.5 h. The reaction mixture was then evaporated and the residue chromatographed on 6 g Lichroprep silica gel Si-60 (25–40 μm) using a 5:1 v/v mixture of toluene and ethyl acetate as eluent. Thus, 4.5 mg (0.014 mmol, yield 60%) of the E- and/or Z-2-cyano-3-methylsulfanyl-3-(1,1,2-tritritio-1,2,4,5-tetrahydro-benzo[d]azepin-3-yl)-acrylic acid ethyl ester was obtained.

2-methyl-6-oxo-4-(1,1,2-tritritio-1,2,4,5-tetrahydro-benzo[d]azepin-3-yl)-1,6-dihydro-pyrimidine-5-carbonitrile A solution of 4.4 mg (0.014 mmol) of Z- and/or E-2-cyano-3-methylsulfanyl-3-(1,1,2-tritritio-1,2,4,5-tetrahydro-benzo[d]azepin-3-yl)-acrylic acid ethyl ester, of 3 mg (0.032 mmol) of acetamidine hydrochloride and of 6.6 mg (0.044 mmol) of 1,8-diazabicyclo[5.4.0]undec-7-ene in 1.0 ml of N,N-dimethylformamide was stirred at 100° C. for 2 hours. The reaction mixture was then partitioned between a 50:1 v/v mixture of dichloromethane and methanol and ice water acidified with about 2 ml 0.2 N hydrogen chloride. The organic phase was dried over anhydrous sodium sulfate. The crude product was chromatographed on 5 g Lichroprep silica gel Si-60 (25–40 μm) using a 6:1 v/v mixture of toluene and methanol as eluent. There was thus obtained 2.2 mg (0.008 mmol, yield 57%) of 2-methyl-6-oxo-4-(1,1,2-tritritio-1,2,4,5-tetrahydro-benzo[d]azepin-3-yl)-1,6-dihydro-pyrimidine-5-carbonitrile.

1-Ethyl-2-methyl-6-oxo-4-(1,1,2-tritritio-1,2,4,5-tetrahydro-benzo[d]azepin-3-yl)-1,6-dihydro-pyrimidine-5-carbonitrile A suspension of 2.2 mg (0.008 mmol) of 2-methyl-6-oxo-4-(1,1,2-tritritio-1,2,4,5-tetrahydro-benzo[d]azepin-3-yl)-1,6-dihydro-pyrimidine-5-carbonitrile, of 16 mg (0.10 mmol) of ethyl iodide and of 4.3 mg (0.031 mmol) of potassium carbonate in 0.21 ml of N,N-dimethylformamide was stirred at room temperature for 3 h. The reaction mixture was then partitioned between ethyl acetate and ice water acidified with about 1 ml 0.2 N hydrochloric acid. The organic phase was dried over anhydrous sodium sulfate. The thus obtained crude product was purified by chromatography on 5 g Lichroprep silica gel Si-60 (15–25 μm) using a 50:1 v/v mixture of dichloromethane and methanol as eluent to yield 1.8 mg (0.0058 mmol, yield 73%) of the 1-ethyl-2-methyl-6-oxo-4-(1,1,2-tritritio-1,2,4,5-tetrahydro-benzo[d]azepin-3-yl)-1,6-dihydro-pyrimidine-5-carbonitrile as colorless solid, MS: [M($^3$H$_0$)+H]$^+$=309 (27%), MS: [M($^3$H$_1$)+H]$^+$=311 (38%), MS: [M($^3$H$_2$)+H]$^+$=313 (27%), MS: [M($^3$H$_3$)+H]$^+$=315 (8%).

EXAMPLE A

Tablets of the following composition are produced in a conventional manner:

| | mg/Tablet |
|---|---|
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in a conventional manner:

| | mg/Tablet |
|---|---|
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

| | mg/capsule |
|---|---|
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:

1. A compound of formula I'

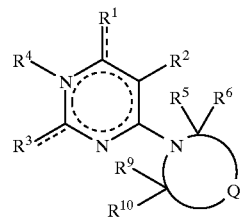

wherein $R^1$ is oxygen, hydroxy, lower alkoxy or 2,2,2-trifluoroethoxy;

$R^2$ is nitro or cyano;

$R^3$ is hydrogen, lower alkyl, oxygen, lower alkoxy, amino, lower alkyl-amino or hydroxy-lower alkyl-amino;

$R^4$ is hydrogen, lower alkyl, lower alkenyl or is absent, if the adjacent nitrogen atom is part of a covalent double bond;

$R^5$, $R^6$, $R^9$ and $R^{10}$ are, independently from each other, hydrogen or lower alkyl;

is selected from the group consisting of

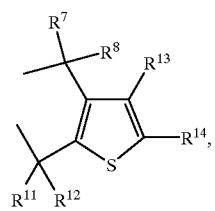

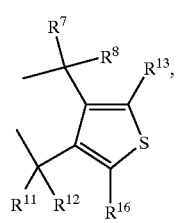

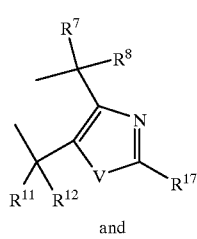
and

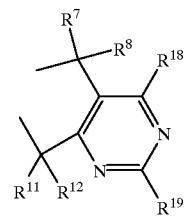

wherein $R^7$, $R^8$, $R^{11}$ or $R^{12}$ are, independently from each other, hydrogen, lower alkyl, or hydroxy;

$R^{13}$ and $R^{14}$ are, independently from each other, hydrogen or lower alkyl;

$R^{15}$ and $R^{16}$ are, independently from each other, hydrogen or lower alkyl;

$R^{17}$ is hydrogen, lower alkyl, lower alkoxy, hydroxy or amino;

$R^{18}$ is hydrogen or hydroxy;

$R^{19}$ is hydrogen, lower alkyl, lower alkoxy, hydroxy or amino;

V is NH, S or O; and a dotted line is an optional bond, or a pharmaceutically acceptable salt of a compound of formula I'.

2. The compound or pharmaceutically acceptable salt according to claim 1, which is a compound of formula I'a

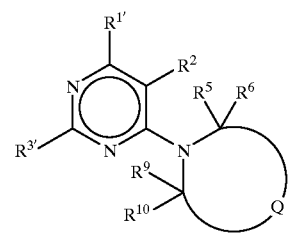

wherein $R^{1'}$ is hydroxy, lower alkoxy or 2,2,2-trifluoroethoxy;

$R^2$ is nitro or cyano;

$R^{3'}$ is hydrogen, lower alkyl, lower alkoxy, amino, lower alkyl-amino or hydroxy-lower alkyl-amino;

$R^5$, $R^6$, $R^9$ and $R^{10}$ are, independently from each other, hydrogen or lower alkyl; and

is selected from the group consisting of

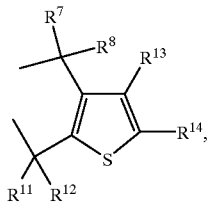
IIa

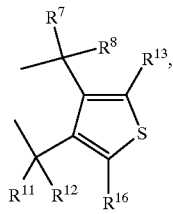
IIb

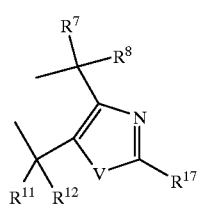
IIc

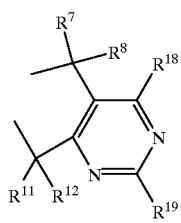
IId wherein
R$^7$, R$^8$, R$^{11}$ or R$^{12}$ are, independently from each other, hydrogen, lower alkyl, or hydroxy;
R$^{13}$ and R$^{14}$ are, independently from each other, hydrogen or lower alkyl;
R$^{15}$ and R$^{16}$ are, independently from each other, hydrogen or lower alkyl;
R$^{17}$ is hydrogen, lower alkyl, lower alkoxy, hydroxy or amino;
R$^{18}$ is hydrogen or hydroxy;
R$^{19}$ is hydrogen, lower alkyl, lower alkoxy, hydroxy or amino; and
V is NH, S or O;

or a pharmaceutically acceptable salt of a compound of formula I'a.

3. The compound or pharmaceutically acceptable salt of claim 2, wherein

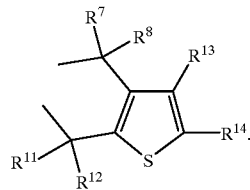 is

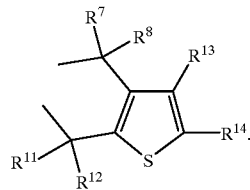
IIa

4. The compound or pharmaceutically acceptable salt of claim 3, wherein R$^2$ is NO$_2$.
5. The compound or pharmaceutically acceptable salt of claim 4, wherein R$^{1'}$ is lower alkoxy.
6. The compound or pharmaceutically acceptable salt of claim 5, wherein R$^{3'}$ is lower alkyl.
7. The compound or pharmaceutically acceptable salt of claim 6, wherein R$^5$, R$^6$, R$^7$, R$^8$, R$^9$, R$^{10}$, R$^{11}$, R$^{12}$, R$^{13}$ and R$^{14}$ are H.
8. The compound or pharmaceutically acceptable salt of claim 7, which is 6-(6-ethoxy-2-methyl-5-nitro-pyrimidin-4-yl)-5,6,7,8-tetrahydro-4H-thieno[2,3-d]azepine.
9. The compound or pharmaceutically acceptable salt of claim 3, wherein R$^{1'}$ is lower alkoxy.
10. The compound or pharmaceutically acceptable salt of claim 2, wherein is

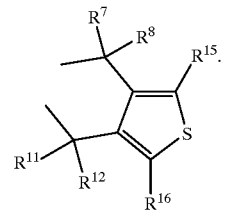
IIb

11. The compound or pharmaceutically acceptable salt of claim 10, wherein R$^2$ is NO$_2$.
12. The compound or pharmaceutically acceptable salt of claim 2, wherein is

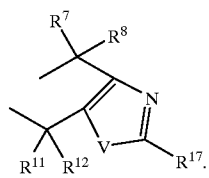
IIc

13. The compound or pharmaceutically acceptable salt of claim 12, wherein R$^2$ is NO$_2$.
14. The compound or pharmaceutically acceptable salt of claim 13, wherein R$^{1'}$ is lower alkoxy.
15. The compound or pharmaceutically acceptable salt of claim 14, wherein V is S.
16. The compound or pharmaceutically acceptable salt of claim 15, wherein R$^{3'}$ is lower alkyl.

17. The compound or pharmaceutically acceptable salt of claim 16, wherein $R^5$, $R^6$, $R^7$, $R^8$, $R^9$, $R^{10}$, $R^{11}$ and $R^{12}$ are H.

18. The compound or pharmaceutically acceptable salt of claim 17, which is 6-(6-ethoxy-2-methyl-5-nitro-pyrimidin-4-yl)-2-methyl-5,6,7,8-tetrahydro-4H-thiazolo[4,5-d]azepine.

19. The compound or pharmaceutically acceptable salt of claim 12, wherein $R^{1'}$ is lower alkoxy.

20. The compound or pharmaceutically acceptable salt of claim 12, wherein V is S.

21. The compound or pharmaceutically acceptable salt of claim 2, wherein

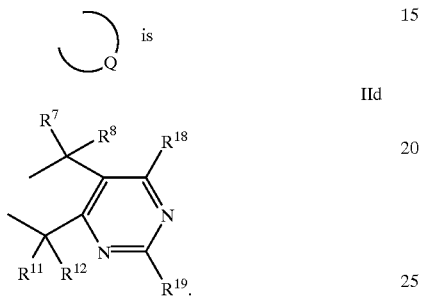

is

22. The compound or pharmaceutically acceptable salt of claim 21, wherein $R^2$ is $NO_2$.

23. The compound or pharmaceutically acceptable salt of claim 22, wherein $R^{1'}$ is hydroxy.

24. The compound or pharmaceutically acceptable salt of claim 23, wherein $R^{3'}$ is lower alkyl.

25. The compound or pharmaceutically acceptable salt of claim 24, wherein $R^5$, $R^6$, $R^7$, $R^8$, $R^9$, $R^{10}$, $R^{11}$ and $R^{12}$ are H.

26. The compound or pharmaceutically acceptable salt of claim 25, wherein $R^{18}$ is hydroxy.

27. The compound or pharmaceutically acceptable salt of claim 26, wherein $R^{19}$ is lower alkyl.

28. The compound or pharmaceutically acceptable salt of claim 27, which is 7-(6-hydroxy-2-methyl-5-nitro-pyrimidin-4-yl)-2-methyl-6,7,8,9-tetrahydro-5H-pyrimido[4,5-d]azepin-4-ol.

29. The compound or pharmaceutically acceptable salt of claim 25, wherein $R^{18}$ and $R^{19}$ are H.

30. The compound or pharmaceutically acceptable salt of claim 29, which is 2-methyl-5-nitro-6-(5,6,8,9-tetrahydro-pyrimido[4,5-d]azepin-7-yl)-pyrimidin-4-ol.

31. The compound or pharmaceutically acceptable salt according to claim 1, which is a compound of formula I'b

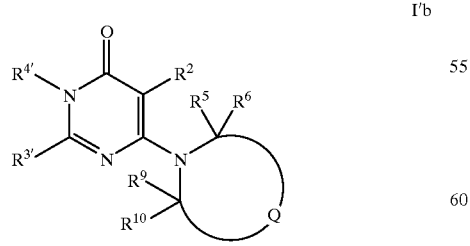

wherein
$R^2$ is nitro or cyano;
$R^{3'}$ is hydrogen, lower alkyl, lower alkoxy, amino, lower alkyl-amino or hydroxy-lower alkyl-amino;

$R^{4'}$ is hydrogen, lower alkyl or lower alkenyl;
$R^5$, $R^6$, $R^9$ and $R^{10}$ are, independently from each other, hydrogen or lower alkyl; and

is selected from the group consisting of

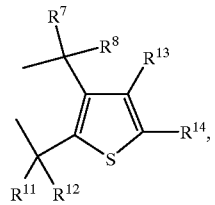
IIa

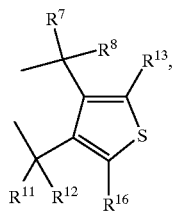
IIb

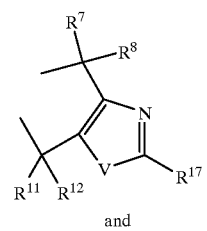
IIc and

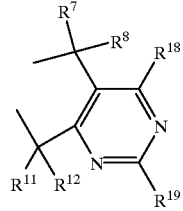
IId wherein
$R^7$, $R^8$, $R^{11}$ or $R^{12}$ are, independently from each other, hydrogen, lower alkyl, or hydroxy;
$R^{13}$ and $R^{14}$ are, independently from each other, hydrogen or lower alkyl;
$R^{15}$ and $R^{16}$ are, independently from each other, hydrogen or lower alkyl;
$R^{17}$ is hydrogen, lower alkyl, lower alkoxy, hydroxy or amino;
$R^{18}$ is hydrogen or hydroxy;
$R^{19}$ is hydrogen, lower alkyl, lower alkoxy, hydroxy or amino; and
V is NH, S or O;
or a pharmaceutically acceptable salt of a compound of formula I'b.

32. The compound or pharmaceutically acceptable salt of claim 31, wherein

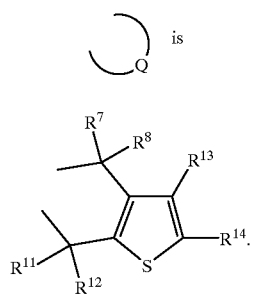

IIa

33. The compound or pharmaceutically acceptable salt of claim 32, wherein $R^2$ is $NO_2$.

34. The compound or pharmaceutically acceptable salt of claim 33, wherein $R^{4'}$ is hydrogen or lower alkyl.

35. The compound or pharmaceutically acceptable salt of claim 34, wherein $R^{3'}$ is lower alkyl.

36. The compound or pharmaceutically acceptable salt of claim 35, wherein $R^5$, $R^6$, $R^7$, $R^8$, $R^9$, $R^{10}$, $R^{11}$, $R^{12}$, $R^{13}$ and $R^{14}$ are H.

37. The compound or pharmaceutically acceptable salt of claim 36, which is 2-methyl-5-nitro-6-(4,5,7,8-tetrahydro-thieno[2,3-d]azepin-6-yl)-3H-pyrimidin-4-one.

38. The compound or pharmaceutically acceptable salt of claim 36, which is 3-ethyl-2-methyl-5-nitro-6-(4,5,7,8-tetrahydro-thieno[2,3-d]azepin-6-yl)-3H-pyrimidin-4-one.

39. The compound or pharmaceutically acceptable salt of claim 35, wherein $R^7$ is hydroxy.

40. The compound or pharmaceutically acceptable salt of claim 39, which is [rac]-6-(4-hydroxy-4,5,7,8-tetrahydro-thieno[2,3-d]azepin-6-yl)-2-methyl-5-nitro-3H-pyrimidin-4-one.

41. The compound or pharmaceutically acceptable salt of claim 31, wherein

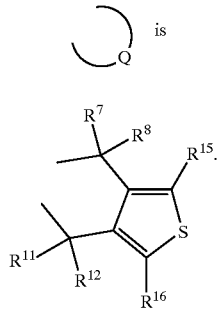

IIb

42. The compound or pharmaceutically acceptable salt of claim 41, wherein $R^2$ is $NO_2$.

43. The compound or pharmaceutically acceptable salt of claim 31, wherein

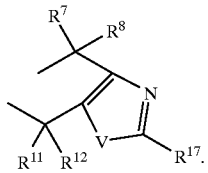

IIc

44. The compound or pharmaceutically acceptable salt of claim 43, wherein $R^2$ is $NO_2$.

45. The compound or pharmaceutically acceptable salt of claim 44, wherein V is S.

46. The compound or pharmaceutically acceptable salt of claim 45, wherein $R^{3'}$ is lower alkyl.

47. The compound or pharmaceutically acceptable salt of claim 46, wherein $R^5$, $R^6$, $R^7$, $R^8$, $R^9$, $R^{10}$, $R^{11}$ and $R^{12}$ are H.

48. The compound or pharmaceutically acceptable salt of claim 47, wherein $R^{17}$ is hydrogen.

49. The compound or pharmaceutically acceptable salt of claim 48, which is 2-methyl-5-nitro-6-(4,5,7,8-tetrahydro-thiazolo[4,5-d]azepin-6-yl)-3H-pyrimidin-4-one.

50. The compound or pharmaceutically acceptable salt of claim 47, wherein $R^{17}$ is lower alkyl.

51. The compound or pharmaceutically acceptable salt of claim 50, which is 2-methyl-6-(2-methyl-4,5,7,8-tetrahydro-thiazolo[4,5-d]azepin-6-yl)-5-nitro-3H-pyrimidin-4-one.

52. The compound or pharmaceutically acceptable salt of claim 50, which is 3-ethyl-2-methyl-6-(2-methyl-4,5,7,8-tetrahydro-thiazolo[4,5-d]azepin-6-yl)-5-nitro-3H-pyrimidin-4-one.

53. The compound or pharmaceutically acceptable salt of claim 47, wherein $R^{17}$ is amino.

54. The compound or pharmaceutically acceptable salt of claim 53, which is 6-(2-amino-4,5,7,8-tetrahydro-thiazolo[4,5-d]azepin-6-yl)-2-methyl-5-nitro-3H-pyrimidin-4-one.

55. The compound or pharmaceutically acceptable salt of claim 53, which is 6-(2-amino-4,5,7,8-tetrahydro-thiazolo[4,5-d]azepin-6-yl)-3-ethyl-2-methyl-5-nitro-3H-pyrimidin-4-one.

56. The compound or pharmaceutically acceptable salt of claim 43, wherein V is S.

57. The compound or pharmaceutically acceptable salt of claim 31, wherein

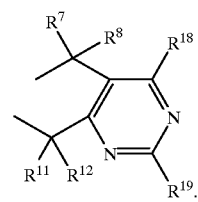

IId

58. The compound or pharmaceutically acceptable salt of claim 57, wherein $R^2$ is $NO_2$.

59. The compound or pharmaceutically acceptable salt according to claim 1, which is a compound of formula I'c

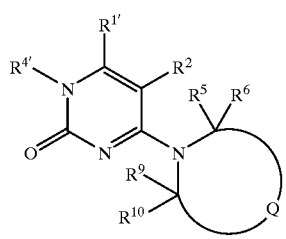

wherein
R$^{1'}$ is hydroxy, lower alkoxy or 2,2,2-trifluoroethoxy;
R$^2$ is nitro or cyano;
R$^{4'}$ is hydrogen, lower alkyl or lower alkenyl;
R$^5$, R$^6$, R$^9$ and R$^{10}$ are, independently from each other, hydrogen or lower alkyl; and

is selected from the group consisting of

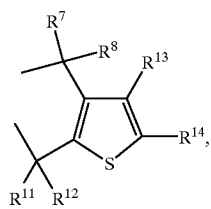
IIa

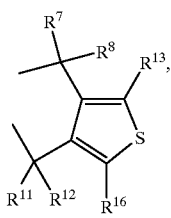
IIb

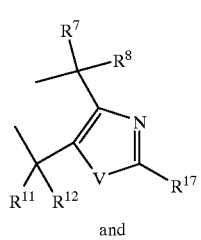
IIc and

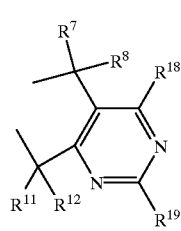
IId wherein
R$^7$, R$^8$, R$^{11}$ or R$^{12}$ are, independently from each other, hydrogen, lower alkyl, or hydroxy;
R$^{13}$ and R$^{14}$ are, independently from each other, hydrogen or lower alkyl;
R$^{15}$ and R$^{16}$ are, independently from each other, hydrogen or lower alkyl;
R$^{17}$ is hydrogen, lower alkyl, lower alkoxy, hydroxy or amino;
R$^{18}$ is hydrogen or hydroxy;
R$^{19}$ is hydrogen, lower alkyl, lower alkoxy, hydroxy or amino; and
V is NH, S or O;
or a pharmaceutically acceptable salt of a compound of formula I'c.

60. The compound or pharmaceutically acceptable salt of claim 59, wherein

 is

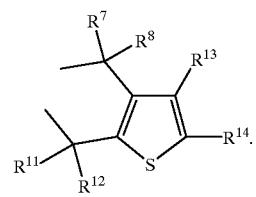
IIa

61. The compound or pharmaceutically acceptable salt of claim 60, wherein R$^2$ is NO$_2$.

62. The compound or pharmaceutically acceptable salt of claim 59, wherein

 is

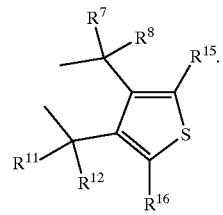
IIb

63. The compound or pharmaceutically acceptable salt of claim 62, wherein R$^2$ is NO$_2$.

64. The compound or pharmaceutically acceptable salt of claim 59, wherein

 is

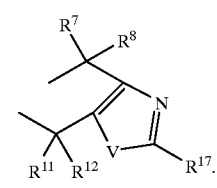
IIc

65. The compound or pharmaceutically acceptable salt of claim 64, wherein R$^2$ is NO$_2$.

66. The compound or pharmaceutically acceptable salt of claim 65, wherein V is S.

67. The compound or pharmaceutically acceptable salt of claim 59, wherein

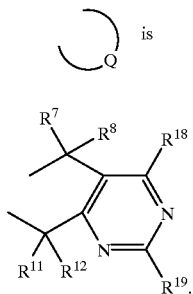

IId

68. The compound or pharmaceutically acceptable salt of claim 25, wherein $R^2$ is $NO_2$.

69. A process for the manufacture of a compound of formula I'

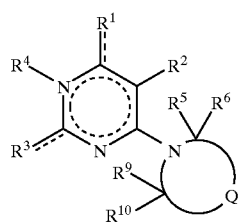

I' wherein
- $R^1$ is oxygen, hydroxy, lower alkoxy or 2,2,2-trifluoroethoxy;
- $R^2$ is nitro or cyano;
- $R^3$ is hydrogen, lower alkyl, oxygen, lower alkoxy, amino, lower alkyl-amino or hydroxy-lower alkyl-amino;
- $R^4$ is hydrogen, lower alkyl, lower alkenyl or is absent, if the adjacent nitrogen atom is part of a covalent double bond;
- $R^5$, $R^6$, $R^9$ and $R^{10}$ are, independently from each other, hydrogen or lower alkyl;

is selected from the group consisting of

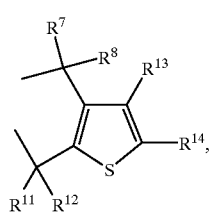

IIa

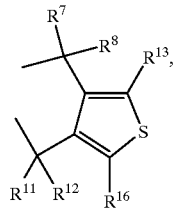

IIb

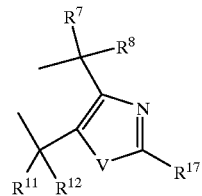

IIc and

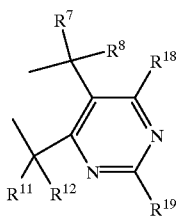

IId wherein
- $R^7$, $R^8$, $R^{11}$ or $R^{12}$ are, independently from each other, hydrogen, lower alkyl, or hydroxy;
- $R^{13}$ and $R^{14}$ are, independently from each other, hydrogen or lower alkyl;,
- $R^{15}$ and $R^{16}$ are, independently from each other, hydrogen or lower alkyl;
- $R^{17}$ is hydrogen, lower alkyl, lower alkoxy, hydroxy or amino;
- $R^{18}$ is hydrogen or hydroxy;
- $R^{19}$ is hydrogen, lower alkyl, lower alkoxy, hydroxy or amino;
- V is NH, S or O; and
- a dotted line is an optional bond, or a pharmaceutically acceptable salt thereof, the process comprising:

a) reacting a compound of the formula III

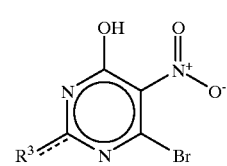

III with a compound of formula IV

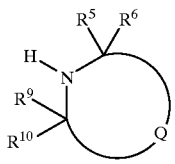
IV in a solvent containing a base to form a compound of formula I-1

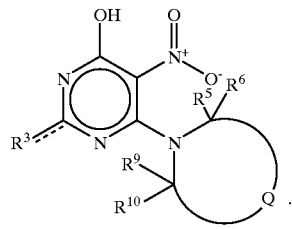
I-1

70. A process for the manufacture of a compound of formula I'

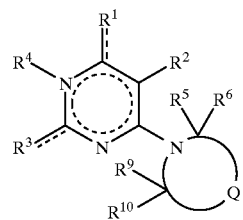
I' wherein $R^1$ is oxygen, hydroxy, lower alkoxy or 2,2,2-trifluoroethoxy;

$R^2$ is nitro or cyano;

$R^3$ is hydrogen, lower alkyl, oxygen, lower alkoxy, amino, lower alkyl-amino or hydroxy-lower alkyl-amino;

$R^4$ is hydrogen, lower alkyl, lower alkenyl or is absent, if the adjacent nitrogen atom is part of a covalent double bond;

$R^5$, $R^6$, $R^9$ and $R^{10}$ are, independently from each other, hydrogen or lower alkyl;

is selected from the group consisting of

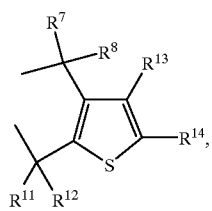
IIa

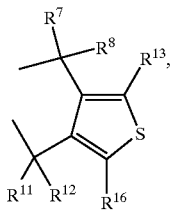
IIb

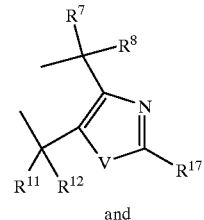
IIc and

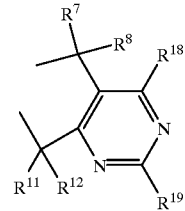
IId wherein $R^7$, $R^8$, $R^{11}$ or $R^{12}$ are, independently from each other, hydrogen, lower alkyl, or hydroxy;

$R^{13}$ and $R^{14}$ are, independently from each other, hydrogen or lower alkyl;

$R^{15}$ and $R^{16}$ are, independently from each other, hydrogen or lower alkyl;

$R^{17}$ is hydrogen, lower alkyl, lower alkoxy, hydroxy or amino;

$R^{18}$ is hydrogen or hydroxy;

$R^{19}$ is hydrogen, lower alkyl, lower alkoxy, hydroxy or amino;

V is NH, S or O; and a dotted line is an optional bond, or a pharmaceutically acceptable salt thereof, the process comprising:

b) alkylating a compound of formula I-2

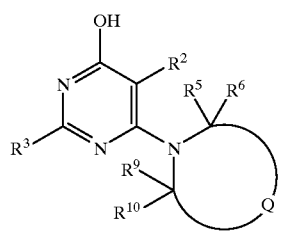
I-2 to form a compound of formula I-3

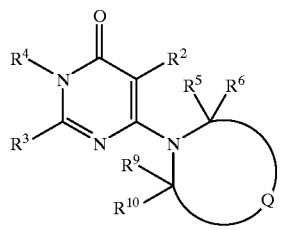

or a compound of formula I-4

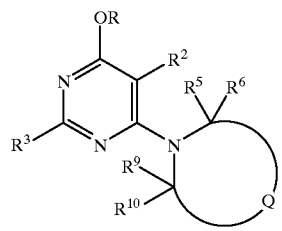

wherein R is hydroxy or lower alkyl.

71. A process for the manufacture of a compound of formula I'

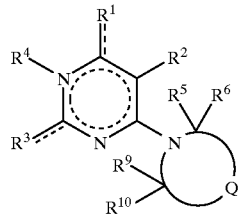

wherein $R^1$ is oxygen, hydroxy, lower alkoxy or 2,2,2-trifluoroethoxy;

$R^2$ is nitro or cyano;

$R^3$ is hydrogen, lower alkyl, oxygen, lower alkoxy, amino, lower alkyl-amino or hydroxy-lower alkyl-amino;

$R^4$ is hydrogen, lower alkyl, lower alkenyl or is absent, if the adjacent nitrogen atom is part of a covalent double bond;

$R^5$, $R^6$, $R^9$ and $R^{10}$ are, independently from each other, hydrogen or lower alkyl;

is selected from the group consisting of

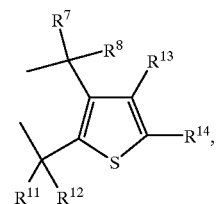

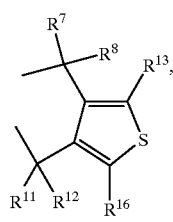

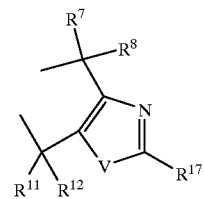

and

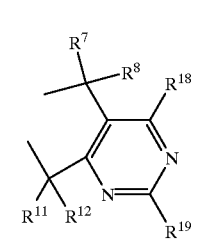

wherein $R^7$, $R^8$, $R^{11}$ or $R^{12}$ are, independently from each other, hydrogen, lower alkyl, or hydroxy;

$R^{13}$ and $R^{14}$ are, independently from each other, hydrogen or lower alkyl;

$R^{15}$ and $R^{16}$ are, independently from each other, hydrogen or lower alkyl;

$R^{17}$ is hydrogen, lower alkyl, lower alkoxy, hydroxy or amino;

$R^{18}$ is hydrogen or hydroxy;

$R^{19}$ is hydrogen, lower alkyl, lower alkoxy, hydroxy or amino;

V is NH, S or O; and a dotted line is an optional bond, or a pharmaceutically acceptable salt thereof, the process comprising:

c) reacting a compound of formula V

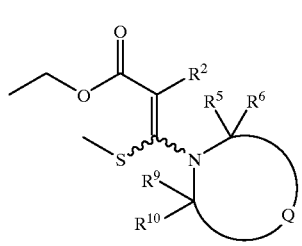

V (Z and/or E)

with a compound of formula VIa

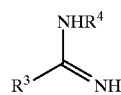

VIa to form a compound of formula I-3

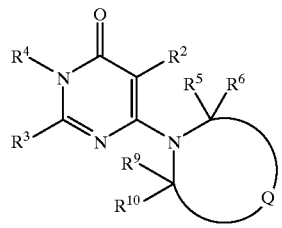

I-3 wherein the step of reacting the compound of formula V with the compound of formula VIa occurs in a solvent selected from the group consisting of N,N-dimethylformamid containing 1,8-diazabicyclo[5.4.0]undec-7-ene, dimethylsulfoxide containing 1,8-diazabicyclo[5.4.0]undec-7-ene and ethanol containing sodium ethylate.

* * * * *

UNITED STATES PATENT AND TRADEMARK OFFICE
CERTIFICATE OF CORRECTION

PATENT NO.    : 6,369,222 B1                                          Page 1 of 3
DATED         : April 9, 2002
INVENTOR(S)   : Alfred Binggeli, Hans-Peter Maerki, Vincent Mutel, Maurice Wilhelm and Wolfgang Wostl It is certified that error appears in the above-identified patent and that said Letters Patent is hereby corrected as shown below:

Title page,
Item [75], Inventors, please insert  -- Maurice Wilhelm, Morschwiller le Bas (FR) --
Item [30], Foreign Application Priority Data - delete "(CH)" and insert -- Europe --

Column 25,
Lines 11-20, delete  " 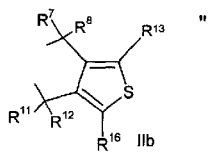 "

and insert

-- 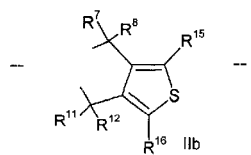 --

Column 28,
Lines 22-30, delete  " 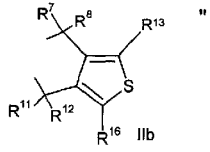 "

and insert

-- 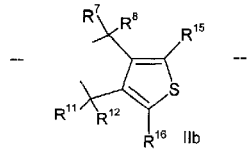 --

Column 31,
Lines 38-46, delete  " 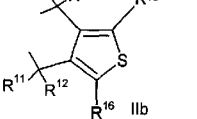 "

and insert

-- 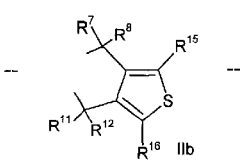 --

UNITED STATES PATENT AND TRADEMARK OFFICE
CERTIFICATE OF CORRECTION

PATENT NO.    : 6,369,222 B1
DATED         : April 9, 2002
INVENTOR(S)   : Alfred Binggeli, Hans-Peter Maerki, Vincent Mutel, Maurice Wilhelm and Wolfgang Wostl It is certified that error appears in the above-identified patent and that said Letters Patent is hereby corrected as shown below:

Column 34,
Lines 1-10, delete " 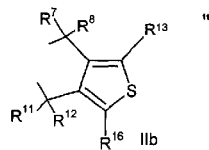 "

and insert

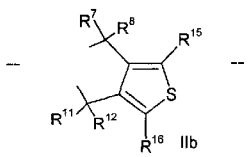 --

Column 38,
Lines 15-23, delete " 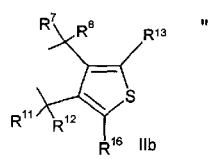 "

and insert

-- 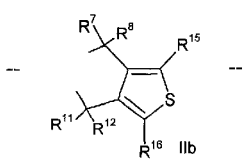 --

Column 34,
Lines 60-65, delete " 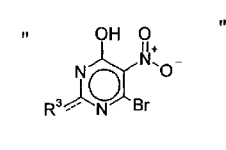 "

and insert

-- 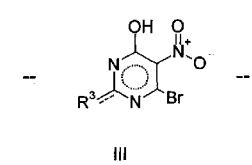 --

UNITED STATES PATENT AND TRADEMARK OFFICE
CERTIFICATE OF CORRECTION

PATENT NO.   : 6,369,222 B1
DATED        : April 9, 2002
INVENTOR(S)  : Alfred Binggeli, Hans-Peter Maerki, Vincent Mutel, Maurice Wilhelm and Wolfgang Wostl It is certified that error appears in the above-identified patent and that said Letters Patent is hereby corrected as shown below:

Column 35,
Lines 13-23, delete " 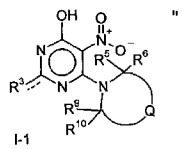 "

and insert

-- 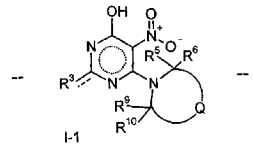 --

Signed and Sealed this

Ninth Day of July, 2002

*Attest:*

*Attesting Officer*

JAMES E. ROGAN
*Director of the United States Patent and Trademark Office*